United States Patent [19]

Foody et al.

[11] Patent Number: 6,090,595
[45] Date of Patent: *Jul. 18, 2000

[54] PRETREATMENT PROCESS FOR CONVERSION OF CELLULOSE TO FUEL ETHANOL

[75] Inventors: Brian Foody; Jeffrey S. Tolan; Jerome D. Bernstein, all of Ottawa; Patrick Foody, Sr., Ville St. Laurent, all of Canada

[73] Assignee: Iogen Corporation, Ottawa, Canada

[ * ] Notice: This patent is subject to a terminal disclaimer.

[21] Appl. No.: 09/207,468

[22] Filed: Dec. 8, 1998

Related U.S. Application Data

[63] Continuation-in-part of application No. 08/871,347, Jun. 9, 1997, Pat. No. 5,916,780.

[51] Int. Cl.$^7$ .............................. C12P 19/14; C12P 7/06; C12P 7/14; C12P 7/10
[52] U.S. Cl. .............................. 435/99; 127/37; 435/105; 435/161; 435/162; 435/163; 435/165; 435/209
[58] Field of Search .............................. 435/99, 105, 161, 435/162, 163, 165, 209; 127/37

[56] References Cited

U.S. PATENT DOCUMENTS

| | | | |
|---|---|---|---|
| 4,237,226 | 12/1980 | Grethlein | 435/99 |
| 4,461,648 | 7/1984 | Foody | 127/37 |
| 4,752,579 | 6/1988 | Arena et al. | 435/99 |
| 5,221,357 | 6/1993 | Brink | 127/43 |
| 5,366,558 | 11/1994 | Brink | 127/43 |
| 5,411,594 | 5/1995 | Brelsford | 127/37 |
| 5,424,417 | 6/1995 | Torget et al. | 536/56 |
| 5,536,325 | 7/1996 | Brink | 127/43 |
| 5,628,830 | 5/1997 | Brink | 127/36 |

OTHER PUBLICATIONS

Grethlein, "Chemical Breakdown of Cellulosic Materials", *J. Appl. Chem. Biotechnol.* 28:296–308 (1978).
Foody, et al., Final Report, "Optimization of Steam Explosion Pretreatment," *U.S. Department of Energy Report*, Contract No. DE–AC02–79ETZ3050 (Apr. 1980).
Fan, et al., "Evaluation of Pretreatments For Enzymatic Conversion of Agricultural Residues," Proceedings Of The Third Symposium On Biotechnology In Energy Production And Conservation (Gatlinburg, Tennessee, May 12–15, 1981).
Cunningham, et al., Proceedings Of The Seventh Symposium On Biotechnology For Fuels And Chemicals (Gatlinburg, Tennessee, May 14–17, 1985).
Grethlein and Converse, "Common Aspects Of Acid Prehydrolysis And Steam Explosion For Pretreating Wood," *Bioresource Technology* 36:77–82 (1991).
Knappert, et al., "Partial Acid Hydrolysis of Cellulosic Materials As A Pretreatment for Enzymatic Hydrolysis," *Biotechnology and Bioengineering* 22:1449–1463 (1980).
Grohmann, et al., "Optimization of Dilute Acid Pretreatment Of Biomass," Seventh Symposium on Biotechnology for Fuels and Chemicals (Gatlinburg, Tennessee, May 14–17, 1985).
Tukey, "Horticulture Is A Great Green Carpet That Covers The Earth," *American Journal of Botany*, 44(3):279–289 (1957).
Thay, "Betting The Transgenic Farm", *Chemical and Engineering News*, Apr. 28, 1997,p. 15–19.
Ghose, "Measurement of Cellulase Activities", *Pure and Appl. Chem.*, 59:2:257–268 (1987).

*Primary Examiner*—Herbert J. Lilling
*Attorney, Agent, or Firm*—Fitzpatrick, Cella, Harper & Scinto

[57] ABSTRACT

An improved pretreatment of cellulosic feedstocks, to enable economical ethanol production by enzyme treatment. The improved pretreatment comprises choosing either a feedstock with a ratio of arabinoxylan to total nonstarch polysaccharides (AX/NSP) of greater than about 0.39, or a selectively bred feedstock on the basis of an increased ratio of AX/NSP over a starting feedstock material, and reacting at conditions that disrupt the fiber structure and hydrolyze a portion of the cellulose and hemicellulose. This pretreatment produces a superior substrate for enzymatic hydrolysis, by enabling the production of more glucose with less cellulose enzyme than any known procedures. This pretreatment is uniquely suited to ethanol production. Preferred feedstocks with an AX/NSP level greater than about 0.39 include varieties of oat hulls and corn cobs.

53 Claims, 2 Drawing Sheets

PRETREATMENT PROCESS FOR CONVERSION OF CELLULOSE TO FUEL ETHANOL

This application is a continuation-in-part of application Ser. No. 08/871,347, filed Jun. 9, 1997, now U.S. Pat. No. 5,916,780.

BACKGROUND OF THE INVENTION

1. Field of the Invention

This invention relates to the production of fuel alcohol from cellulose. More specifically, this invention relates to the pretreatment of cellulose feedstocks for ethanol production. The pretreatment reaction of feedstocks chosen with a ratio of arabinan plus xylan to non-starch polysaccharides (AX/NSP) of greater than about 0.39 produces a superior substrate for enzymatic hydrolysis than other feedstocks. These pretreated feedstocks are uniquely suited to ethanol production. Examples of feedstocks that could be chosen in such a pretreatment process include some varieties of oat hulls and corn cobs, and feedstocks selectively bred for high AX/NSP.

2. Brief Description of the Prior Art

The possibility of producing ethanol from cellulose has received much attention due to the availability of large amounts of feedstock, the desirability of avoiding burning or landfilling the materials, and the cleanliness of the ethanol fuel. The advantages of such a process for society are described, for example in a cover story of the *ATLANTIC MONTHLY*, (April 1996).

The natural cellulosic feedstocks for such a process typically are referred to as "biomass." Many types of biomass, including wood, agricultural residues, herbaceous crops, and municipal solid wastes, have been considered as feedstocks for ethanol production. These materials primarily consist of cellulose, hemicellulose, and lignin. This invention is concerned with converting the cellulose to ethanol. The familiar corn starch-to-ethanol process, in which the starch is converted to ethanol using sulfurous acid and amylase enzymes, lies outside the scope of this invention.

Cellulose is a polymer of the simple sugar glucose connected by beta 1,4 linkages. Cellulose is very resistant to degradation or depolymerization by acid, enzymes, or micro-organisms. Once the cellulose is converted to glucose, the resulting sugar is easily fermented to ethanol using yeast. The difficult challenge of the process is to convert the cellulose to glucose.

The oldest methods studied to convert cellulose to glucose are based on acid hydrolysis (review by Grethlein, *Chemical Breakdown Of Cellulosic Materials*, J. APPL. CHEM. BIOTECHNOL. 28:296–308 (1978)). This process can involve the use of concentrated or dilute acids. The concentrated acid process uses 72%, by weight, sulfuric acid or 42%, by weight, hydrochloric acid at room temperature to dissolve the cellulose, followed by dilution to 1% acid and heating to 100° C. to 120° C. for up to three hours to convert cellulose oligomers to glucose monomers. This process produces a high yield of glucose, but the recovery of the acid, the specialized materials of construction required, and the need to minimize water in the system are serious disadvantages of this process. Similar problems are encountered when concentrated organic solvents are used for cellulose conversion.

The dilute acid process uses 0.5% to 2%, by weight, sulfuric acid at 180° C. to 240° C. for several minutes to several hours. BRINK (U.S. Pat. Nos. 5,221,537 and 5,536,325) describes a two-step process for the acid hydrolysis of lignocellulosic material to glucose. The first (mild) step depolymerizes the hemicellulose to xylose and other sugars. The second step depolymerizes the cellulose to glucose. The low levels of acid overcome the need for chemical recovery. However, the maximum glucose yield is only about 55% of the cellulose, and a high degree of production of degradation products can inhibit the fermentation to ethanol by yeast. These problems have prevented the dilute acid hydrolysis process from reaching commercialization.

To overcome the problems of the acid hydrolysis process, cellulose conversion processes have been developed using two steps: (1) a pretreatment, and (2) a treatment comprising enzymatic hydrolysis. The purpose of pretreatment is not to hydrolyze the cellulose completely to glucose but, rather, to break down the integrity of the fiber structure and make the cellulose more accessible to attack by cellulase enzymes in the treatment phase. After a typical pretreatment of this type, the substrate has a muddy texture. Pretreated materials also look somewhat similar to paper pulp, but with shorter fibers and more apparent physical destruction of the feedstock.

The goal of most pretreatment methods is to deliver a sufficient combination of mechanical and chemical action, so as to disrupt the fiber structure and improve the accessibility of the feedstock to cellulase enzymes. Mechanical action typically includes the use of pressure, grinding, milling, agitation, shredding, compression/expansion, or other types of mechanical action. Chemical action typically includes the use of heat (often steam), acid, and solvents. Several known pretreatment devices will be discussed below, and with specific reference to extruders, pressurized vessels, and batch reactors.

A typical treatment by enzymatic hydrolysis is carried out by mixing the substrate and water to achieve a slurry of 5% to 12%, by weight of cellulose, and then adding cellulase enzymes. Typically, the hydrolysis is run for 24 to 150 hours at 50° C., pH 5. At the end of the hydrolysis, glucose, which is water soluble, is in the liquid while unconverted cellulose, lignin, and other insoluble portions of the substrate remain in suspension. The glucose syrup is recovered by filtering the hydrolysis slurry; some washing of the fiber solids is carried out to increase the yield of glucose. The glucose syrup is then fermented to ethanol by yeast, and the ethanol recovered by distillation or other means. The ethanol fermentation and recovery are by well-established processes used in the alcohol industry.

The two-step process of pretreatment plus enzyme hydrolysis overcomes many of the problems associated with a single harsh acid hydrolysis. The specific action of the enzymes decreases the amount of degradation products and increases the yield of glucose. In addition, the fact that the pretreatment for fiber destruction is milder than that for cellulose hydrolysis means that lower chemical loadings can be used, decreasing the need for chemical recovery, and a lower amount of degradation products are made, increasing the yield and decreasing the inhibition of fermentation to ethanol by yeast.

Unfortunately, to date the approach of a pretreatment and an enzyme hydrolysis treatment has not been able to produce glucose at a sufficiently low cost, so as to make a fermentation to ethanol commercially attractive. Even with the most efficient currently known pretreatment processes, the amount of cellulase enzyme required to convert the cellulose to glucose is so high as to be cost-prohibitive for ethanol production purposes.

Several approaches have been taken to attempt to decrease the amount of cellulase enzyme required.

The approach of simply adding less cellulase to the system decreases the amount of glucose produced to an unacceptable extent.

The approach of decreasing the amount of enzyme required by increasing the length of time that the enzyme acts on the feedstock leads to uneconomical process productivity, stemming from the high cost of hydrolysis tanks.

The approach of reducing the amount of cellulase enzyme required by carrying out cellulose hydrolysis simultaneously with fermentation of the glucose by yeast is also inefficient. The so-called simultaneous saccharification and fermentation (SSF) process is not yet commercially viable because the optimum operating temperature for yeast, 28° C., is too far below the optimum 50° C. conditions required by cellulase. Operating a SSF system at a compromise temperature of 37° C. is also inefficient, and invites microbial contamination.

The desire for a cost-effective ethanol production process has motivated a large amount of research into developing effective pretreatment systems. Such a pretreatment system would achieve all of the advantages of current pretreatments, including low production of degradation products and low requirements for chemical recovery, but with a sufficiently low requirement for cellulase enzymes so as to make the process economical.

The performance of a pretreatment system is characterized strictly by the amount of enzyme required to hydrolyze an amount of cellulose to glucose. Pretreatment A performs better than pretreatment B, if A requires less enzyme to produce a given yield of glucose than B.

The early work in pretreatment focused on the construction of a working device and determination of the conditions for the best performance.

One of the leading approaches to pretreatment is by steam explosion, using the process conditions described by FOODY (U.S. Pat. No. 4,461,648), which is incorporated herein by reference. In the FOODY process, biomass is loaded into a vessel known as a steam gun. Up to 1% acid is optionally added to the biomass in the steam gun or in a presoak. The steam gun is then filled very quickly with steam and held at high pressure for a set length of time, known as the cooking time. Once the cooking time elapses, the vessel is depressurized rapidly to expel the pretreated biomass, hence the terminology "steam explosion" and "steam gun".

In the FOODY process, the performance of the pretreatment depends on the cooking time, the cooking temperature, the concentration of acid used, and the particle size of the feedstock. The recommended pretreatment conditions in the FOODY process are similar for all the cellulosic feedstocks tested (hardwood, wheat straw, and bagasse) provided they are divided into fine particles. Furthermore, the cooking temperature is determined by the pressure of the saturated steam fed into the steam gun. Therefore, the practical operating variables that effect the performance of the pretreatment are the steam pressure, cooking time, and acid concentration. The FOODY process describes combinations of these variables for optimum performance; as one might expect, increasing the time decreases the temperature used, and vice versa. The range of steam pressure taught by FOODY is 250 psig to 1000 psig, which corresponds to temperatures of 208° C. to 285° C.

Another published study of steam explosion pretreatment parameters is Foody, et al, Final Report, *Optimization of Steam Explosion Pretreatment*, U.S. DEPARTMENT OF ENERGY REPORT ET230501 (April 1980). This study reported the effects of the pretreatment variables of temperature (steam pressure), particle size, moisture content, pre-conditioning, die configuration, and lignin content. The optimized steam explosion conditions were reported for three types of straws, five species of hardwood, and four crop residues.

The optimum pretreatment conditions as published by FOODY were subsequently confirmed by others using other feedstocks and different equipment. For example, GRETHLEIN (U.S. Pat No. 4,237,226), describes pretreatment of oak, newsprint, poplar, and corn stover by a continuous plug-flow reactor, a device that is similar to an extruder. Rotating screws convey a feedstock slurry through a small orifice, where mechanical and chemical action break down the fibers.

GRETHLEIN specifies required orifice sizes, system pressures, temperatures (180° C. to 300°C.), residence times (up to 5 minutes), acid concentrations (up to 1% sulfuric acid) and particle sizes (preferred 60 mesh). GRETHLEIN obtained similar results for all of the specified substrates he identified (See Column 3, line 30). Even though the GRETHLEIN device is quite different from the steam gun of FOODY, the time, temperature, and acid concentration for optimum performance are similar.

More recent work has focused on understanding the means by which pretreatment improves the enzymatic hydrolysis of a given substrate. BRINK (U.S. Pat. No. 5,628,830) describes the pretreatment of lignocellulosic material by using a steam process to break down the hemicellulose and following with hydrolysis of the cellulose using cellulase enzymes.

The first explanation offered to characterize the advantage of a pretreatment was that a pretreatment should be evaluated on the amount of lignin removed, with better performance associated with higher degrees of delignification. See Fan, Gharpuray, and Lee, *Evaluation Of Pretreatments For Enzymatic Conversion Of Agricultural Residues*, PROCEEDINGS OF THE THIRD SYMPOSIUM ON BIOTECHNOLOGY IN ENERGY PRODUCTION AND CONSERVATION, (Gatlinburg, Tenn., May 12–15, 1981). The notion that delignification alone characterizes pretreatment was also reported by Cunningham, et al, PROCEEDINGS OF THE SEVENTH SYMPOSIUM ON BIOTECHNOLOGY FOR FUELS AND CHEMICALS, (Gatlinburg, Tenn., May 14–17, 1985).

Grethlein and Converse, *Common Aspects of Acid Prehydrolysis and Steam Explosion for Pretreating Wood*, BIORESOURCE TECHNOLOGY 36(2):77–82 (1991), put forth the proposition that the degree of delignification is important only for previously dried substrates and, therefore, not a relevant consideration to most pretreatment processes that use undried feedstocks.

Knappert, et al, *A Partial Acid Hydrolysis of Cellulosic Materials as a Pretreatment for Enzymatic Hydrolysis*, BIOTECHNOLOGY AND BIOENGINEERING 23:1449–1463 (1980) reported that the increased susceptibility to enzyme hydrolysis after pretreatment is caused by the creation of micropores by the removal of the hemicellulose, a change in crystallinity of the substrate, and a gross reduction in the degree of polymerization of the cellulose molecule.

Grohmann, et al, *Optimization of Dilute Acid Pretreatment of Biomass*, SEVENTH Symposium ON BIOTECHNOLOGY FOR FUELS AND CHEMICALS (Gatlinburg, Tenn., May 14–17, 1985) specifically supported one of the hypotheses of Knappert, et al by showing that removal of hemicellulose in pretreatment results in improved enzymatic hydrolysis of the feedstock. (See p.59–80). Grohmann, et al worked with wheat straw and aspen wood at temperatures of 95° C. to 160° C. and cooking times of up to 21 hours. For both feedstocks, about 80% of the cellulose was digested by cellulase enzymes after optimum pretreatments, in which 80% to 90% of the xylan was removed from the initial material.

Grohmann and Converse also report ed that the crystallinity index of the cellulose was not changed significantly by pretreatment. They further reported that pretreatments can create a wide range of degrees of polymerization while resulting in similar susceptibility to enzymatic hydrolysis.

Another alternative explanation offered for the improvements in enzymatic hydrolysis due to pretreatment is the increase in surface area of the substrate. Grethlein and Converse refined this explanation by showing that the surface area that is relevant is that which is accessible to the cellulase enzyme, which has a size of about 51 angstroms. The total surface area, which is measured by the accessibility of small molecules such as nitrogen, does not correlate with the rate of enzymatic hydrolysis of the substrate, for the reason that small pores that do not allow the enzyme to penetrate do not influence the rate of hydrolysis.

In spite of a good understanding of devices and optimum conditions for pretreatment, and a large quantity of research into the mechanism of a pretreatment process, there still does not exist an adequate pretreatment for a commercially feasible process to convert cellulosic materials to ethanol. Such a pretreatment process would be of enormous benefit in bringing the cellulose-to-ethanol process to commercial viability.

SUMMARY OF THE INVENTION

Figure 1:
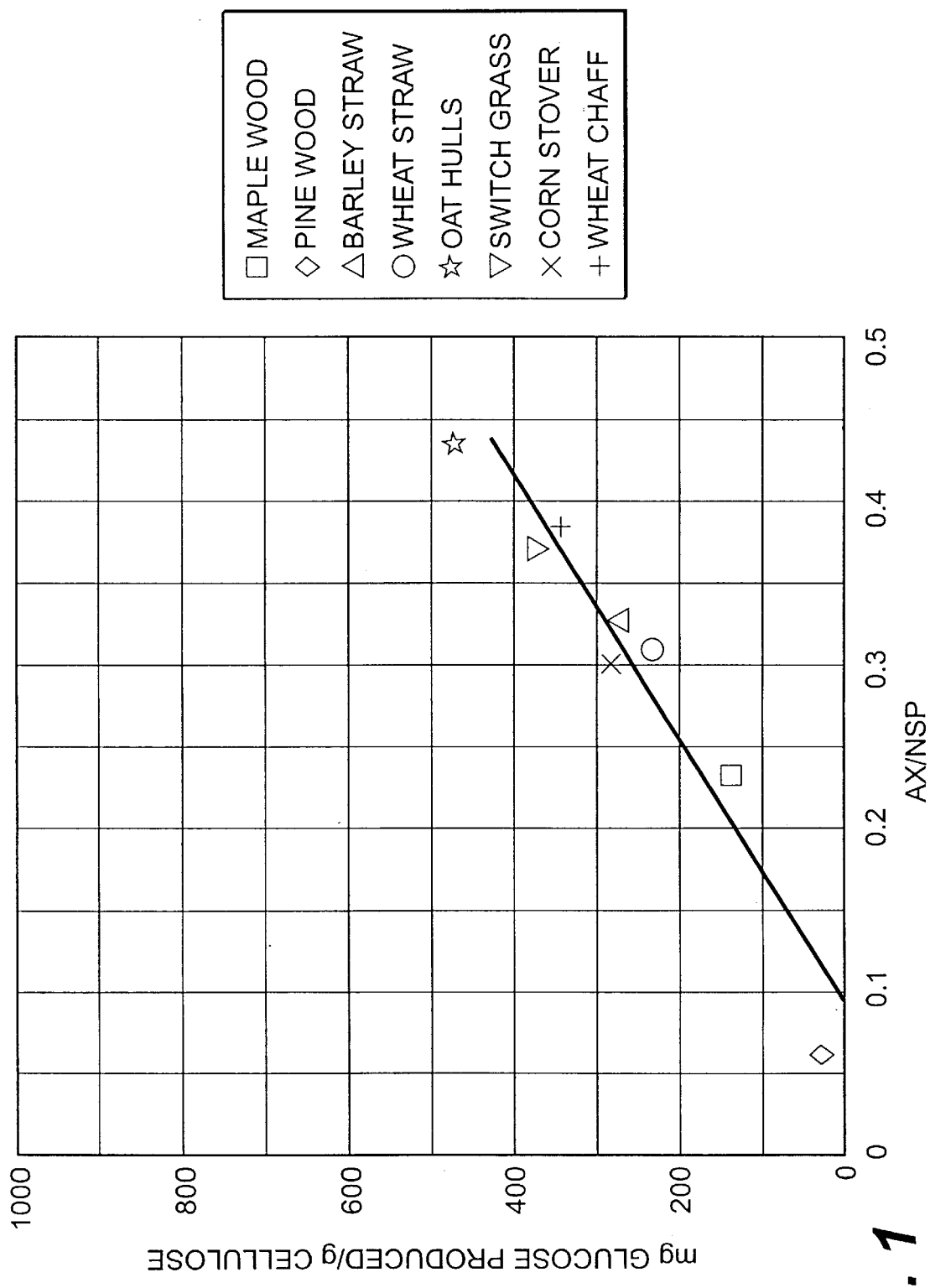
FIG. 1. A graph of cellulose conversion for certain feedstocks after pretreatment reaction at 121° C., as a function of AX/NSP of the initial material, according to EXAMPLE 3.

The inventors have discovered that a critical property of a feedstock determines its relative cellulase enzyme requirement to convert the cellulose to glucose after the pretreatment reaction. That property is the ratio of arabinan plus xylan to total nonstarch polysaccharides, which we will refer to hereinafter as "AX/NSP." The inventors have discovered that the higher the AX/NSP, the less cellulase enzyme is required after the pretreatment reaction, and hence the more economical the production of ethanol. Feedstocks with AX/NSP over about 0.39 are particularly well suited for a cellulose-to-ethanol process. Examples of such feedstocks are certain varieties of oat hulls and corn cobs.

Based on this discovery, the inventors have developed improved pretreatment processes prior to enzyme treatment that converts a lignocellulosic feedstock to ethanol. One such process consists essentially of the steps:
1. Choosing a lignocellulosic feedstock with a ratio of arabinan plus xylan to total nonstarch polysaccharides (abbreviated AX/NSP) of greater than 0.39.
2. Reacting the chosen feedstock at conditions which disrupt the fiber structure and effect an hydrolysis upon portions of both cellulose and hemicellulose, so as to improve digestibility of the pretreated feedstock by a subsequent cellulase enzyme treatment.

A second such process consists essentially of the steps:
1. Choosing a lignocellulosic feedstock selectively bred to have a relatively increased ratio of arabinan plus xylan to total nonstarch polysaccharides (AX/NSP).
2. Reacting the chosen feedstock at conditions which disrupt the fiber structure and effect an hydrolysis upon portions of both cellulose and hemicellulose, so as to improve digestibility of the pretreated feedstock by a subsequent cellulase enzyme treatment.

Once a feedstock is chosen based on high AX/NSP, the pretreatment reactions can be carried out in a manner consistent with previous reports. This might include single stage or two stage reactions in steam guns, extruders, or other devices used previously.

By choosing the feedstock based on AX/NSP, the resulting cellulase enzyme requirement after the pretreatment reaction is significantly lower than otherwise required. This results in significant savings in the cost of producing ethanol from lignocellulosic materials.

There have been no previous reports of the superior performance after pretreatment of feedstocks specifically chosen because of any particular level of AX/NSP, let alone an AX/NSP level that is greater than 0.39, by weight.

The present invention is very surprising in view of the U.S. D.O.E. study by FOODY, et al, supra, which observed no correlation between xylan content of the feedstocks and glucose yield after steam explosion and hydrolysis by cellulase.

FOODY, et al was a study of thirteen feedstocks. The resulting conversion of cellulose to glucose varied widely among the pretreated feedstocks, between 46% to 50% for oak and sunflower stalks to 86% to 87% for barley straw and maple. The two best feedstocks of FOODY et al, barley straw and maple wood, had xylan contents of 31% and 19%, respectively, which were among the highest and lowest values reported. Oak and aspen both contained 21% xylan, yet they achieved widely differing glucose yields after hydrolysis by cellulase, 46% and 72%, respectively.

The present invention also is very surprising in view of the patent to GRETHLEIN, supra. GRETHLEIN described a device for the pretreatment of feedstocks using dilute sulfuric acid All four of the GRETHLEIN feedstocks (oak, newsprint, poplar, and corn stover) performed similarly (Column 3, lines 25 to 32). This reported result is exactly contrary to the teachings of the present invention, who have found and identified a novel feedstock property, AX/NSP, that can reliably be used to predict the performance of the feedstocks after treatment.

The present invention also is very surprising in view of the publication by Knappert, et al., supra, which reviewed four feedstocks: Solka floc, newsprint, oak, and corn stover. Knappert, et al obtained optimum yields of glucose from cellulose after pretreatment reactions. One hundred percent yield was obtained from newsprint, corn stover, and oak, and 81% yield was obtained from Solka floc (Tables I and II, page 1453–1457). As the only feedstocks with cellulose and xylan content reported were newsprint and Solka floc, this study simply does not address the relationship between AX/NSP of the feedstock and the digestibility of the material by cellulase enzymes after pretreatment reaction.

The present invention actually suggests that the teachings of Knappert, et al are incorrect. At the very least, the teachings of Knappert, et al are at odds with the teachings of the present invention. Knappert et al taught that a low hemicellulose content of a material presages little improvement in cellulose digestibility during pretreatment. The present invention, at EXAMPLE 5, shows a large improvement in the digestibility of oat hulls with pretreatment reaction after the hemicellulose has been removed by a mild reaction.

SUMMARY OF TERMINOLOGY

The invention and preferred embodiments described hereafter are to be construed using certain terms as hereafter defined, for purposes of the present invention.

Lignocellulosic feedstock means any raw material that one might consider for a cellulose-to-ethanol process. Such a material has at least about 25% cellulose, and the cellulose is substantially converted to glucose and then ethanol in the process. Typical lignocellulosic feedstocks materials are wood, grains, and agricultural waste. For the present purposes there are no specifications on the lignin, starch, protein, or ash content. Examples of lignocellulosic feedstocks that have been considered for an ethanol process are wood, grasses, straws, and crop waste. Often, a lignocellulosic feedstock originates from one species of fiber. However, for present purposes the lignocellulosic feedstock can be a mixture that originates from a number of different species.

Conversion to fuel ethanol denotes the conversion of at least about 40% of the cellulose to glucose, and then fermentation of the glucose to ethanol. For the present purposes there are no specifications on the conversion products made from the lignin or the hemicellulose. In a preferred embodiment, at least 60% of the cellulose is converted to glucose and fermented to ethanol.

Xylan and xylan content are the terms used to express the quantity of anhydroxylose present in the feedstock. Much of the anhydroxylose is present as a linear beta 1,4-linked polysaccharide of xylose, but the designation xylan is not limited to anhydroxylose of this structure.

Arabinan and arabinan content are the terms used to express the quantity of anhydroarabinose present in the feedstock. Much of the anhydroarabinose is present as a branched alpha 1,3-linked polysaccharide of arabinose, but the designation arabinan is not limited to anhydroarabinose of this structure.

Arabinan plus xylan refers to the sum of the arabinan content and the xylan content of the feedstock. This is distinguished from the term arabinoxylan, which refers to an alpha 1,3-linked polymer of arabinose and xylose. Arabinoxylan is a specific example of arabinan and xylan, but does not comprise all possible forms of arabinan and xylan.

Hemicellulose is a general term that includes all natural polysaccharides except cellulose and starch. The term includes polymers of xylose, arabinose, galactose, mannose, etc. and mixtures thereof. In the present work, the primary constituents of the hemicellulose are arabinose and xylose.

AX/NSP is the ratio of arabinan plus xylan to non-starch polysaccharides and can be measured for any feedstock based on the analytical procedures described herein. AX/NSP is calculated from EQUATION (1):

$$AX/NSP=(xylan+arabinan)/(xylan+arabinan+cellulose) \quad (1)$$

where the xylan, arabinan, and cellulose contents of the feedstocks are measured according to the procedures in EXAMPLE 1 and AX/NSP is calculated as shown in EXAMPLE 1.

AX/NSP is taught herein to characterize the performance of the pretreatment. The higher the AX/NSP, the less cellulase enzyme is required to hydrolyze the cellulose to glucose after a given pretreatment. The pretreatment performance is particularly good for feedstocks with AX/NSP of greater than about 0.39. This point is illustrated in EXAMPLES 3 and 4.

The AX/NSP content should be measured for each batch of a feedstock used, as it will no doubt vary seasonally and with the age, geographical location, and cultivar of the feedstock. Therefore, there are no absolute values of AX/NSP that are always valid for a given species. However, samples of oat hulls and corn cobs exhibited the highest AX/NSP in the data collected, as well as the highest performance in pretreatment. Oat hulls and corn cobs from the lots sampled would therefore be preferred feedstocks for an ethanol process.

The theoretical upper limit of AX/NSP is 0.75. This would be present in a material that was 25% cellulose and 75% arabinan plus xylan. The inventors know of no materials with this composition. The highest AX/NSP observed by the inventors is 0.422 .

The hemicellulose, cellulose, arabinan, and xylan content of various materials have been widely published. However, the analytical methods used can greatly influence the apparent composition, and these publications are often based on widely varying methods. Therefore, these publications can be relied on only to give a general idea as to the approximate composition of these materials. For the purposes of practicing the invention, the same analytical methods must be applied to each candidate feedstock, and those of Example 1 are preferred for the absolute values being claimed.

In practicing the invention, feedstocks with high AX/NSP can be identified by two generic methods: (1) by screening of natural fibers and grains, and (2) by screening of varieties selectively bred for higher AX/NSP levels.

Reaction or Pretreatment reaction refers to a chemical process used to modify a lignocellulosic feedstock to make it more amenable to hydrolysis by cellulase enzymes. In the absence of pretreatment, the amount of cellulase enzyme required to produce glucose is impractical.

Improve digestibility by cellulose enzymes by disrupting the fiber structure and effecting the hydrolysis of a portion of the hemicellulose and the cellulose. This terminology refers to the physical and chemical changes to the feedstock caused by the pretreatment reaction. At a minimum, pretreatment increases the amount of glucose hydrolyzed from the feedstock by cellulase, disrupts the fibers, and hydrolyzes some fraction of the cellulose and hemicellulose.

The pretreatment process of the invention preferably is part of an integrated process to convert a lignocellulosic feedstock to ethanol. Such a process includes, after pretreatment, enzymatic hydrolysis of cellulose to glucose, fermentation of the glucose to ethanol, and recovery of the ethanol.

Cellulose hydrolysis refers to the use of cellulase enzymes to convert the pretreated cellulose to glucose. In the present invention, a minority of the cellulose is hydrolyzed during the pretreatment, and the majority survives pretreatment and is subjected to hydrolysis by cellulase enzymes. The manner in which the enzymatic hydrolysis is carried out is not constrained by the invention, but preferred conditions are as follows. The hydrolysis is carried out in a slurry with water that is initially 5% to 12% cellulose and is maintained at pH 4.5 to 5.0 and 50° C. The cellulase enzymes used might be any of the commercial cellulases available, which are manufactured by IOGEN CORPORATION, NOVO NORDISK, GENENCOR INTERNATIONAL, PRIMALCO, and other companies. The cellulase enzymes might be supplemented with beta-glucosidase to complete the conversion of cellobiose to glucose. A commercial beta-glucosidase enzyme is NOVOZYM 188, sold by NOVO NORDISK.

The skilled practitioner will realize that the amount of cellulase enzyme used in the hydrolysis is determined by the cost of the enzyme and the desired hydrolysis time, glucose yield, and glucose concentration, all of which are influenced by the process economics and will vary as each of the relevant technologies is evaluated. The typical enzyme dosage range is 1 to 50 Filter Paper Units (FPU) cellulase per gram cellulose for 12 to 128 hours. In a preferred embodiment the cellulase enzyme dosage is 1 to 10 FPU per gram cellulose. EXAMPLES 2 and 3 describe cellulose hydrolysis in more detail.

In a preferred embodiment, cellulose hydrolysis and ethanol fermentation are carried out simultaneously, using those techniques generally employed in an SSF process, as discussed previously herein.

Ethanol fermentation and recovery are carried out by conventional processes that are well known, such as yeast fermentation and distillation. The invention is not constrained by the manner in which these operations are carried out.

DESCRIPTION OF PREFERRED EMBODIMENTS

In practicing the invention, any type of feedstock, including but not limited to naturally occurring and selectively bred feedstock, can be employed. As emphasized above, the novelty of the present invention relates to the use of a high AX/NSP ratio, heretofore unrecognized as a critical standard for choosing optimum feedstocks for glucose and ethanol production; the origin of the feedstock is of secondary importance.

In one embodiment, the feedstock is naturally occurring. In this case, the AX/NSP of the feedstock is measured by the method of Example 1. Feedstocks with AX/NSP of greater than about 0.39 are preferred for a cellulose-to-ethanol process.

The AX/NSP content should be measured for each batch of a feedstock used, as it will no doubt vary seasonally and with age, geographic location, and cultivar of the feedstock. As experience with a given feedstock accumulates, the frequency of testing AX/NSP will lessen.

In a preferred embodiment, the feedstock is not corn fiber (also known as corn kernel hulls).

In a preferred embodiment, the starch content of the feedstock is less than 10%. Feedstocks with more than this level of starch will have severe sugar degradation in a pretreatment process designed for cellulose, and are better suited to glucose production using amylase enzymes. Starch content is measured by the method described in Example 1.

In a more preferred embodiment, the starch content of the feedstock is less than 7%.

In another preferred embodiment, the feedstock has already been selectively bred. In this case, the AX/NSP of the bred feedstock is measured by the method of Example 1 and compared with that of the natural feedstock. If the AX/NSP has been increased by breeding, the feedstock is more suitable for cellulose conversion than the natural or starting feedstock material.

Such breeding can, in principle, be carried out by any of the common methods used to select for desired traits in plant breeding. These methods are summarized by H. B. Tukey, "Horticulture is a Great Green Carpet that Covers the Earth" in American Journal of Botany 44(3):279–289 (1957) and Ann M. Thayer, "Betting the Transgenic Farm" in Chemical and Engineering News, Apr. 28, 1997, p. 15–19. The methods include:

1. Scientific Breeding. Screen varieties of a species for a high level of AX/NSP and repeatedly grow those varieties which exhibit the trait.
   Selective breeding protocols directed to obtaining species that have a high level of AX/NSP may involve enhancing the levels of xylan within the species.
2. Chimeras. Graft two or more species and screen the resulting species for the level of AX/NSP.
3. Pollination breeding. Combine two or more species by cross pollination and screen for AX/NSP level.
4. Chemical thinning. Expose plants to chemical toxins such that only the fittest survive. Requires a toxin that is resisted by arabinan or xylan.
5. Induction. Expose species to conditions that induce higher levels of AX/NSP.
6. Environmental distress. Expose species to conditions that induce death unless protested by high levels of AX/NSP.
7. Nutrition and fertilizers. Develop nutritional regimen to increase AX/NSP.
8. Genetic engineering. Genetically modify a species so as to increase its level of AX/NSP. Specifically, the production of transgenic plants that express genes that result in high levels of AX/NSP within the plant. For example, such genetic modification may include, but is not limited to, genes encoding enzymes involved in enhancing the levels of xylan within the species. Constructs comprising genes of interest can be introduced into plant cells using for example, Ti plasmids, Ri plasmids, plant virus vectors, direct DNA transformation, microinjection, electroporation, etc. (Miki and Iyer, *Fundamentals of Gene Transfer in Plants.* In *Plant Metabolism,* 2d Ed. D T Dennis, D H Turpin, D D Lefebrve, D B Layzell (Eds.), Addison Wesly, Langmans Ltd. London, pp. 561–579 (1997).)

In one preferred embodiment, the selectively bred feedstock is corn, oats, wheat, sugar cane, or a component of these. These materials are well suited to ethanol production and are widely available.

In another preferred embodiment, the selectively bred feedstock is a C4 grass. C4 grasses are so classified by their pathway of carbon dioxide metabolism, which involves intermediates with 4 carbon atoms. This is described in Biology of Plants, by Raven, Evert, and Curtis, Worth Publishing Co., second edition, 1976, pages 116–117.

Of the C4 grasses, preferred feedstocks are C4 perennial grasses. The perennial grasses do not require yearly planting and fertilization and are therefore more suitable for ethanol production than annual grasses.

Of the C4 perennial grasses, the most preferred are switch grass, miscanthus, cord grass, and rye grass. These grasses are particularly fast growing. Cord grass is classified as a C4 grass even though a portion of its growth cycle uses C3 metabolism.

In another preferred embodiment, the selectively bred lignocellulosic feedstock has an AX/NSP level that is greater than about 0.39, and such a selectively bred feedstock then is reacted to increase its digestibility by cellulase enzymes and converted to ethanol by hydrolyzing the cellulose to glucose with cellulase enzymes, fermenting the glucose, and recovering the ethanol.

In another preferred embodiment, the selectively bred lignocellulosic feedstock has an increased AX/NSP level over a starting feedstock material, but still below 0.39. Such a selectively bred feedstock is then reacted to increase its digestibility to cellulase enzymes and converted to ethanol.

The reason that increasing the AX/NSP content of a feedstock is beneficial, even if the level remains below 0.39, is that in certain geographical areas the climate supports the growth of only a narrow range of feedstocks. For example, corn does not grow in climates where the annual number of [degree] days above 40° F. is less than 240. In these cooler areas, the choice of feedstocks is limited, and there might not be any feedstocks available with AX/NSP close to 0.39. In these climates, improving such a feedstock by selectively breeding to increase its AX/NSP over a starting feedstock material would improve the efficiency of a cellulose-to-ethanol plant significantly, even if the AX/NSP still remained below 0.39. In these situations, the present invention would provide a novel standard against which such selectively bred feedstocks could be measured and compared.

The desired extent of pretreatment might be achieved by any means available, including but not limited to those discussed in the preferred embodiments or examples contained herein. Any combination of mechanical and chemical treatments that results in the chemical changes noted lies within the scope of practicing the invention. This includes any reactors, chemicals added, temperature, time, particle size, moisture, and other parameters that result in the changes to the feedstock.

In a first preferred embodiment, the pretreatment reaction is carried out at the broad conditions described by GRETHLEIN for acid pretreatments. This is done by subjecting the chosen feedstock to a temperature of about 180° C. to about 270° C., for a period of 5 seconds to 60 minutes. It is understood by those skilled in the art that the feedstock temperature is that of the feedstock itself, which might differ from the temperature measured outside the reaction chamber. It is also understood by those skilled in the art that a temperature range specified over a time period is the average temperature for that period, taking into account the effect of temperature on the rate of reaction. For example, the reaction chamber might require a short period to heat from ambient conditions up to 180° C. Based on knowledge of reaction kinetics (for example, within limited temperature ranges for a given substance, the rate approximately doubles over a 10° C. increase in temperature), the effect of the temperature increase on the overall reaction can be calculated and thereby the average temperature determined.

The pretreatment reaction is typically run with 0.1% to 2% sulfuric acid present in the hydrolysis slurry. However, those skilled in the art are aware that alkali or acid present in some feedstocks can alter the acid requirement to be outside of the typical range. The degree of acidity present is better expressed by the target pH range, which is 0.5 to 2.5 regardless of the acid or concentration used. EXAMPLE 8 illustrates pretreatment reactions at this range of conditions.

A second preferred embodiment uses the narrower set of conditions identified by FOODY as optimal for steam explosion pretreatment. This is illustrated in EXAMPLE 4 with pretreatment consisting of a cooking step at a temperature between 220° C. to 270° C. at pH 0.5 to 2.5 for 5 seconds to 120 seconds. Devices used to carry out this pretreatment preferably include sealed batch reactors and continuous extruders. Large scale examples of these pretreatment conditions are described in EXAMPLES 6 and 7.

A third preferred embodiment uses a two-stage pretreatment, whereby the first stage improves the cellulose hydrolysis somewhat while solubilizing primarily the hemicellulose but little cellulose. The second stage then completes a full pretreatment. In this embodiment, the first stage reaction is run at a temperature of less than 180° C. while the second stage reaction is run at a temperature of greater than 180° C. An advantage of a two-stage pretreatment, as shown hereafter in EXAMPLE 5, is that a separate recovery of the hemicellulose for downstream processing is facilitated.

In the third preferred embodiment, the first stage of reaction is carried out at a temperature of about 60° C. to about 140° C. for 0.25 to 24 hours at pH 0.5 to 2.5. More preferably, the first stage of pretreatment is carried out at a temperature of 100° C. to 130° C. for 0.5 to 3 hours at pH 0.5 to 2.5.

In the fourth preferred embodiment, the second stage of reaction is carried out at a temperature of 180° C. to 270° C., at pH 0.5 to 2.5 for a period of 5 seconds to 120 seconds. The feedstock also can be dry (free from added moisture) or in a slurry with water.

Another aspect to successful practice of the present invention is to integrate the pretreatment process within a process that hydrolyzes the pretreated feedstock with cellulase enzymes to produce glucose. In a preferred embodiment, at least 40% of the cellulose in the pretreated feedstock is hydrolyzed by cellulase enzymes to produce glucose. The glucose produced can be purified, crystallized, and packaged as solid sugar. Alternatively, it can be left dissolved in a liquid slurry for further processing or use.

EXAMPLE 1: MEASUREMENT OF AX/NSP IN FEEDSTOCKS

The ratio of arabinan plus xylan to total non-starch polysaccharides of a given feedstock was determined based on a compositional analysis of the feedstocks. This analysis was performed, as follows.

Feedstocks examined were barley straw, wheat straw, wheat chaff, oat hulls, switch grass, corn stover, maple wood, pine wood, and three varieties of corn cobs. All were obtained locally in Ottawa, Ontario except the oat hulls, which were from Quaker Oats in Peterborough, Ontario. The feedstocks were coarsely ground in a Waring blender and then milled through a #20 gauge screen using a Wiley mill. The feedstocks were stored at ambient temperature in sealed bags until the time of use. The moisture content of small samples was 5% to 10% and was determined by drying at 100° C.

Approximately 0.3 grams of sample was weighed into test tubes, each containing 5 ml of 70% sulfuric acid. The tubes were vortex mixed, capped, and placed in a 50° C. water bath for one hour, with vigorous vortex mixing every 10 minutes. After the one hour incubation, the tube contents were transferred into preweighed 250 ml flasks containing 195 ml deionized water, which reduced the acid content to 1.75%. The contents were mixed, and then 10 gram aliquots were transferred into test tubes. The tubes were vortex mixed and then transferred to a steam autoclave, where they were maintained for 1 hour at 121° C. After autoclaving, the solution contents were neutralized using a small amount of barium carbonate, and then vacuum-filtered over glass microfiber filter paper.

The concentrations of glucose, xylose, and arabinose present in the filtrates were measured by using a Dionex Pulse-Amperometric HPLC. These measurements were then related to the weight of the initial sample of feedstock present and expressed as glucan, xylan, and arabinan contents, respectively, of the feedstock, with small adjustments to take into account (1) the water of hydration to make the monomers from polymers and (2) the amount of material destroyed by the concentrated acid, which was measured by taking pure cellulose, xylose, and arabinose controls through the procedure. The determination was performed in triplicate and the average value is reported.

The cellulose content was determined by subtracting the starch content from the total glucan. The starch content was determined by adding 1 gram of Wiley-milled feedstock to a 250 ml flask containing 20 ml of deionized water, 0.2 ml of 91.7 g/L $CaCl_2 \cdot 2H_2O$ stock solution, and 50 microliters of a 1:100 solution of Sigma Alpha Amylase #A3403 in deionized water. Each flask was adjusted to pH 6.4 to 6.6 using dilute sodium hydroxide, then incubated in a boiling water bath for one hour. The flasks were incubated for 30 minutes in a steam autoclave at 121° C. after the addition of a second 50 ml dose of amylase. Finally, the flask was incubated for another 60 minutes in the boiling water bath with a third 50 ml dose of amylase. The flasks were then cooled to ambient temperature and adjusted to pH 4.2 to 4.4 using dilute hydrochloric acid. A 0.5 ml aliquot of Novo Spritamylase stock solution was added; the stock solution consisted of 3 grams of enzyme in 100 ml deionized water. The flasks were shaken at 50° C. for 20 hours with 150 RPM agitation. The flasks were then cooled and the contents were filtered over glass microfiber filter paper. The glucose concentration was then measured on a Yellow Springs Instrument (YSI) glucose analyzer and used to determine the starch concentration of the feedstock, taking into account the water necessary to hydrolyze the starch.

The protein and ash content of the feedstocks were determined by standard Kjeldahl nitrogen and ash oven methods.

The lignin content of the samples was determined by measuring the amount of insoluble solids remaining after the sulfuric acid treatment of the feedstocks, then subtracting the amount of ash present.

The results of these measurements are shown in TABLE 1. The material recovered was between 842 and 1019 mg per gram of original solids (mg/g). This corresponds to 84.2%, by weight, to 101.9% of the starting material, which is typical mass balance closure in these systems.

The AX/NSP content of the feedstocks is shown in TABLE 2. Of the 11 feedstocks analyzed, four have AX/NSP of greater than about 0.39. These include the samples of oat hulls and corn. The other seven feedstocks have AX/NSP content below about 0.39.

TABLE 2

AX/NSP COMPOSITION OF THE FEEDSTOCKS

| Feed-stock | Cellulose (mg/g) (1) | AX (mg/g) (2) | NSP (mg/g) (3) | AX/NSP |
|---|---|---|---|---|
| Barley Straw | 407 | 189 | 596 | 0.317 |
| Wheat Straw | 455 | 190 | 645 | 0.295 |
| Wheat chaff | 391 | 236 | 627 | 0.376 |
| Switch grass | 399 | 222 | 621 | 0.357 |
| Corn stover | 408 | 163 | 571 | 0.285 |
| Maple wood | 500 | 155 | 655 | 0.237 |
| Pine wood | 648 | 47 | 695 | 0.068 |
| Corn cobs (red) | 402 | 291 | 693 | 0.420 |
| Corn cobs (white) | 411 | 288 | 699 | 0.412 |
| Corn cobs (Indian) | 429 | 276 | 705 | 0.391 |
| Oat Hulls | 392 | 286 | 678 | 0.422 |

(1) Cellulose = Glucan − Starch
(2) AX = Xylan + Arabinan
(3) NSP = Xylan + Arabinan + Cellulose

EXAMPLE 2: MEASUREMENT OF CELLULASE ACTIVITY OF AN ENZYME

The cellulase activity of an enzyme is measured using the procedures of Ghose, PURE AND APPL. CHEM.,

TABLE 1

COMPOSITION OF THE FEEDSTOCKS

Measured composition (mg/g)

| Feedstock | Glucan | Starch | Xylan | Arabinan | Lignin | Ash | Protein | Total |
|---|---|---|---|---|---|---|---|---|
| Barley Straw | 426 | 19.6 | 161 | 28 | 168 | 82 | 64 | 929 |
| Wheat Straw | 464 | 8.6 | 165 | 25 | 204 | 83 | 64 | 1005 |
| Wheat chaff | 405 | 14.4 | 200 | 36 | 160 | 121 | 33 | 955 |
| Switch grass | 403 | 3.4 | 184 | 38 | 183 | 48 | 54 | 910 |
| Corn stover | 411 | 3.2 | 128 | 35 | 127 | 60 | 81 | 842 |
| Maple wood | 504 | 4.0 | 150 | 5 | 276 | 6 | 6 | 947 |
| Pine wood | 649 | 1.0 | 33 | 14 | 320 | 0 | 2 | 1018 |
| Corn cobs (red) | 436 | 34 | 253 | 38 | ND (2) | ND | ND | ND |
| Corn cobs (white) | 439 | 28 | 250 | 38 | ND | ND | ND | ND |
| Corn cobs (Indian) | 438 | 8.5 | 240 | 36 | ND | ND | ND | ND |
| Oat Hulls | 481 | 89 | 247 | 39 | 170 | 44 | 38 | 1019 |

(1) Total = Glucan + Xylan + Arabinan + Lignin + Ash + Protein
(2) ND = Not determined 59:257–268 (1987), as follows. A 50 mg piece of Whatman #1 filter paper is placed in each test tube with 1 ml of 50 mM sodium dtrate buffer, pH 4.8. The filter paper is rolled up and the test tube is vortex mixed to immerse the filter paper in the liquid. A dilution series of the enzyme is prepared with concentrations ranging between 1:200 and 1:1600 of the initial strength in 50 mM sodium citrate buffer, pH 4.8. The dilute enzyme stocks and the substrates are separately preheated to 50° C., then a 0.5 ml aliquot of each dilute enzyme stock is placed in a test tube with substrate. The test tubes are incubated for 60 minutes at 50° C. The reaction is terminated by adding 3 ml of dinitrosalicyclic acid (DNS) reagent to each tube and then boiling for 10 minutes. Rochelle salts and deionized water were added to each tube to develop the color characteristic of the reaction between reducing sugars and DNS reagent. The amount of sugar produced by each sample of enzyme is measured, taking into account the small background from the enzyme and the filter paper, by comparing the amount of sugar in each tube with that of known sugar standards brought through the reaction.

A unit of filter paper activity is defined as the number of micromoles of sugar produced per minute. The activity is calculated using the amount of enzyme required to produce 2 mg of sugar. A sample of Iogen Cellulase was found to have 140 filter paper units per ml, as shown in TABLE 3.

TABLE 3

FILTER PAPER ACTIVITY OF IOGEN CELLULASE

| Amount of enzyme (ml) to make 2 mg sugar | Enzyme activity (FPU/ml) |
|---|---|
| 0.00264 | 140.0 |

EXAMPLE 3: MILD PRETREATMENT REACTION WITH THE FEEDSTOCKS

This example illustrates the comparative performance of the feedstocks after a mild pretreatment reaction that primarily dissolves the hemicellulose. This pretreatment reaction by itself is not optimal, although it could be the first stage of a two-stage pretreatment reaction. This mild reaction illustrates the use of AX/NSP to characterize the suitability of a feedstock for ethanol production. Optimized pretreatment reactions are described in later examples.

Samples of 4 grams of Wiley-milled feedstocks from EXAMPLE 1 were placed in 96 grams of 1% sulfuric acid (pH 0.6 to 0.9) in a 250 ml flask. The contents of the flasks were gently mixed, and then the flasks were placed in a steam autoclave at 121° C. for 1 hour. The flasks were then cooled and vacuum-filtered over glass microfiber filter paper. The glucose, xylose, and arabinose concentrations of selected filtrates were determined by neutralizing with barium carbonate and analyzing the samples using a Dionex Pulsed-Amperometric HPLC. The filter cakes were washed with tap water and air dried. The cellulose, xylan, and arabinan concentrations in the solids were determined by dissolution of aliquots in 70% sulfuric acid, as described in EXAMPLE 1.

The effect of the reaction on the cellulose and hemicellulose levels in the selected feedstocks is shown in TABLE 4. In all cases, small amounts (less than 8%) of the cellulose is hydrolyzed, while more than 70% of the hemicellulose is hydrolyzed.

TABLE 4

EFFECT OF 121° C. PRETREATMENT REACTION ON DIFFERENT FEEDSTOCKS
Dissolution (%)

| Feedstock | Cellulose | Hemicellulose |
|---|---|---|
| Barley straw | 3.2 | 85 |
| Wheat straw | 3.6 | 72 |
| Wheat chaff | <2 | 75 |
| Switch grass | 5.7 | 80 |
| Corn stover | 4.3 | 82 |
| Maple wood | <2 | 80 |
| Oat hulls | 7.9 | 85 |

All 11 pretreated feedstocks were subjected to cellulase enzyme hydrolysis as follows. A sample of the pretreated solids corresponding to 0.2 grams of cellulose was added to a 250 ml flask with 19.8 grams of 0.05 M sodium citrate buffer, pH 5.0. Iogen Cellulase (standardized to 140 FPU/ml) and Novozym 188 beta-glucosidase (1440 BGU/ml) were added to the flask in an amount corresponding to 9 FPU/gram cellulose and 125 BGU/gram cellulose. The small amount of glucose carried into the flask with the beta-glucosidase was taken into account.

Each flask was placed on a New Brunswick gyratory shaker at 50° C. and shaken for 20 hours at 250 RPM. At the end of this period, the flask contents were filtered over glass micro fiber filter paper, and the glucose concentration in the filtrate was measured by a YSI glucose analyzer. The glucose concentration was related to the cellulose concentration of the pretreated feedstock to determine the cellulose conversion.

FIG. 1 is a graph of cellulose conversion for certain feedstocks, as a function of AX/NSP, at an average temperature of 121° C., according to EXAMPLE 3.

Surprisingly, as shown in FIG. 1, for this particular pretreatment reaction the cellulose conversion increases linearly with the AX/NSP of the initial feedstock. The four feedstocks with the highest AX/NSP (oat hulls and the three corn cobs) had the highest conversion to glucose.

These results indicate that the higher the AX/NSP of the feedstock, the more suitable the feedstock will be for ethanol production after a given pretreatment.

EXAMPLE 4: HIGH PERFORMANCE PRETREATMENT REACTION WITH THE FEEDSTOCKS

This example illustrates the comparative performance of the feedstocks after a pretreatment reaction. This pretreatment reaction is at conditions that optimize performance in the subsequent cellulose hydrolysis.

Samples of 0.28 grams of Wiley-milled feedstocks from EXAMPLE 1 were placed in 7 grams of 1% sulfuric acid (pH 0.6 to 0.9) in a sealed stainless steel "bomb" reactor. The capacity of the bomb reactor is 9 ml. For any one experiment, five bombs of identical contents were set up and the reaction products were combined to produce a pool of adequate quantity with which to work. The bombs were placed in a preheated 290° C. oil bath for 50 seconds, then removed and cooled by placing them in tap water. Thermocouple measurements showed that the temperature in the interior of the bomb reached 260° C. by the end of the heating period. The average equivalent temperature was 235° C.

The contents of the bombs were removed by rinsing with tap water, and then vacuum-filtered over glass microfiber filter paper. The filter cakes were washed with tap water and air dried. The cellulose concentration in the solids was determined by dissolution of aliquots in 70% sulfuric acid, as described in EXAMPLE 1.

The reacted feedstocks were subjected to hydrolysis by cellulase as follows. A sample of the reacted solids corresponding to 0.05 grams of cellulose was added to a 25 ml flask with 4.9 grams of 0.05 M sodium citrate buffer, pH 4.8. Iogen Cellulase (140 FPU/ml) and Novozym 188 beta-glucosidase (1440 BGU/ml) were added to the flask in an amount corresponding to 9 FPU/gram cellulose and 125 BGU/gram cellulose. The small amount of glucose carried into the flask with the beta-glucosidase was taken into account.

Each flask was placed on an Orbit gyratory shaker at 50° C. and shaken for 20 hours at 250 RPM. At the end of this period, the contents of the flasks were filtered over glass microfiber filter paper, and the glucose concentration in the filtrate was measured by a Dionex Pulsed-Amperometric HPLC. The glucose concentration was related to the cellulose concentration in the pretreated feedstock to determine the cellulose conversion.

Figure 2:
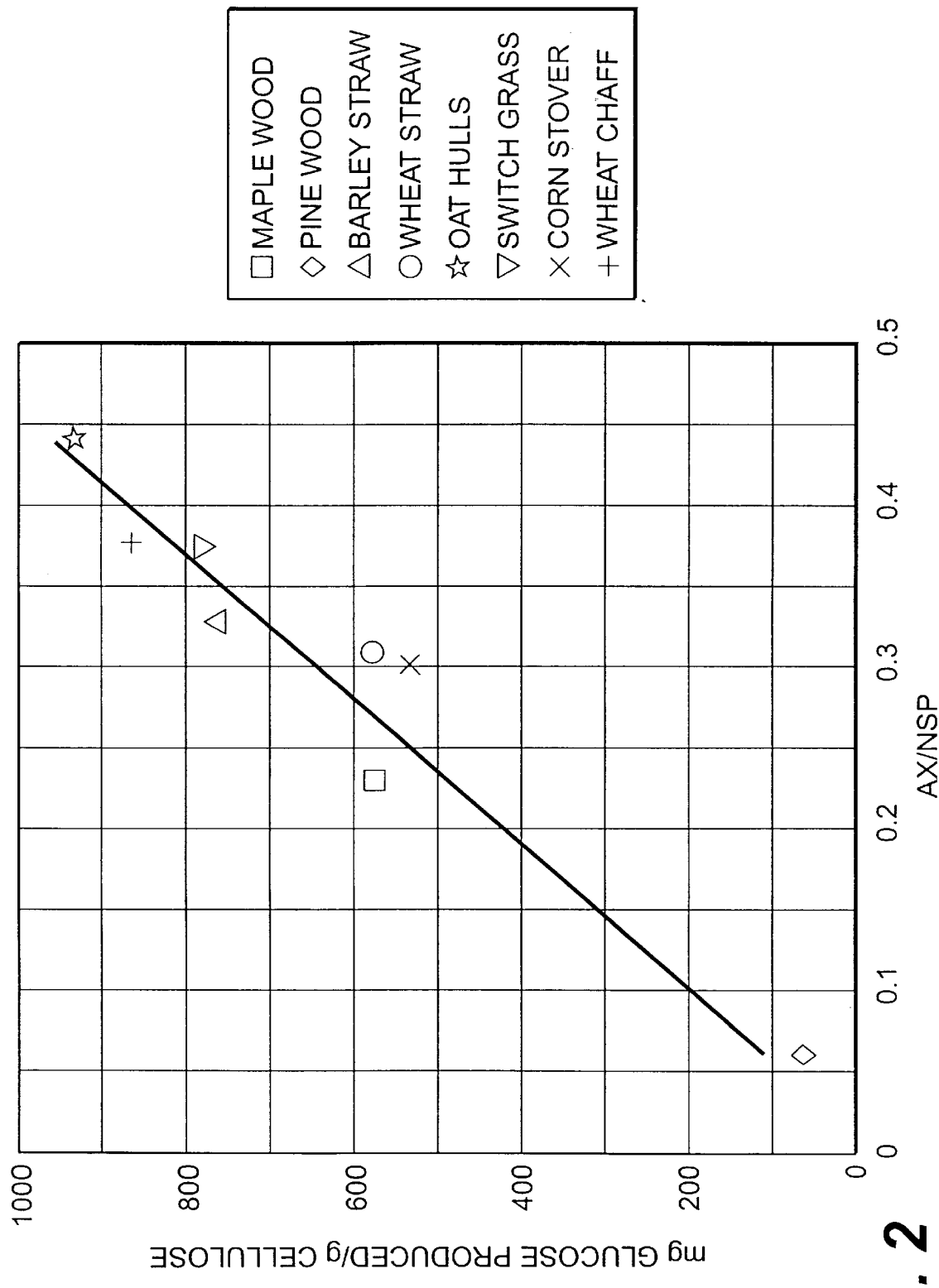
FIG. 2. A graph of cellulose conversion for certain feedstocks after pretreatment reaction at 230° C., as a function of AX/NSP of the initial material, according to EXAMPLE 4.

FIG. 2 is a graph of cellulose conversion for certain feedstocks, as a function of AX/NSP, at an average temperature of 235° C., according to EXAMPLE 4.

As with the 121° C. reaction, FIG. 2 shows a cellulose conversion that also increases linearly with the AX/NSP of the initial feedstock. The four feedstocks with the highest AX/NSP (oat hulls and the three corn cobs) had the highest level of cellulose conversion observed, with more than 65% of the cellulose hydrolyzed to glucose.

These results demonstrate that the higher the AX/NSP of the feedstock, the more suitable the feedstock will be for ethanol production after a high performance pretreatment.

TABLE 5 shows the amount of cellulase enzyme required to reach 80% conversion to glucose. The amount of enzyme required is a key factor in determining the feasibility of an ethanol production process. The data in TABLE 5, are derived from the results shown in FIG. 2 plus other data describing cellulose conversion as a function of cellulase dosage.

The top four feedstocks, including oat hulls and corn cobs, require 23% to 68%, less cellulase enzyme to convert to cellulose to glucose than the next best feedstock: wheat chaff. The top four feedstocks have a great performance advantage over the other feedstocks tested.

The top four feedstocks have AX/NSP greater than 0.39, while the other feedstocks have AX/NSP below this value. This data demonstrates that significantly less cellulase enzyme is required for feedstocks with AX/NSP above about 0.39. This lower enzyme requirement is a significant advantage in an ethanol production process.

TABLE 5

CELLULASE ENZYME REQUIREMENTS

| Feedstock | Cellulase dosage (FPU/g) for 80% conversion in 20 hr | AX/NSP |
|---|---|---|
| Corn Cobs (Red) | 6.6 | 0.420 |
| Corn cobs (White) | 8.7 | 0.412 |
| Corn cobs (Indian) | 15.6 | 0.391 |
| Oat hulls | 16.3 | 0.422 |
| Wheat chaff | 21.0 | 0.376 |

TABLE 5-continued

CELLULASE ENZYME REQUIREMENTS

| Feedstock | Cellulase dosage (FPU/g) for 80% conversion in 20 hr | AX/NSP |
|---|---|---|
| Switch grass | 27.1 | 0.357 |
| Barley straw | 28.3 | 0.317 |
| Wheat straw | 44.5 | 0.295 |
| Maple wood | 45.5 | 0.237 |
| Corn stover | 63.4 | 0.285 |

EXAMPLE 5: TWO-STAGE PRETREATMENT REACTION OF OAT HULLS

This example demonstrates the use of a two-stage pretreatment reaction of oat hulls, the first mild stage followed by a second harsher stage.

For the first stage, samples of 4 grams of Wiley-milled feedstocks from EXAMPLE 1 were placed in 96 grams of 1% sulfuric acid (pH 0.6 to 0.9) in a 250 ml flask. The contents of the flasks were gently mixed, and then the flasks were placed in a steam autoclave at 121° C. for 40 minutes. The flasks were then cooled and vacuum-filtered over glass microfiber filter paper. The glucose, xylose, and arabinose concentrations of the filtrates were determined by neutralizing with barium carbonate and analyzing the samples by using a Dionex Pulsed-Amperometric HPLC. The filter cakes were washed with tap water and air dried. The cellulose, xylan, and arabinan concentrations in the solids were determined by dissolution of aliquots in 70% sulfuric acid, as described in EXAMPLE 1. The effect of the mild reaction on the cellulose and hemicellulose (arabinan+xylan) levels in the feedstock is shown in TABLE 6. Almost all of the hemicellulose is dissolved, which enriches the concentration of cellulose.

TABLE 6

COMPOSITION OF OAT HULLS AFTER MILD PRETREATMENT REACTION

| Feedstock: Oat hulls | Cellulose (%) | Hemicellulose (%) |
|---|---|---|
| Before Pretreatment | 27.9 | 22.0 |
| After Pretreatment | 39.5 | 3.0 |

Samples of 0.28 grams of feedstocks reacted under mild conditions were placed in 7 grams of 1% sulfuric acid (pH 0.6 to 0.9) in a sealed stainless steel "bomb" reactor as described in EXAMPLE 4. Five bombs of identical contents were set up and the reaction products were combined to produce a pool of adequate quantity with which to work. The bombs were placed in a preheated 290° C. oil bath for 50 seconds, then removed and cooled by placing them in tap water.

The contents of the bombs were removed by rinsing with tap water, and then vacuum-filtered over glass microfiber filter paper. The filter cakes were washed with tap water and air dried. The cellulose concentration in the solids was determined by dissolution of aliquots in 70% sulfuric acid, as described in EXAMPLE 1.

After one or two stages of pretreatment reaction, various feedstocks were subjected to hydrolysis by cellulase, as follows. A sample of the pretreated solids corresponding to 0.05 grams of cellulose was added to a 25 ml flask with 4.9 grams of 0.05 M sodium citrate buffer, pH 4.8. Iogen Cellulase (140 FPU/ml) and Novozym 188 beta-glucosidase (1440 BGU/ml) were added to the flask in an amount corresponding to 10 FPU/gram cellulose and 125 BGU per gram cellulose. The small amount of glucose carried into the flask with the beta-glucosidase was taken into account.

Each flask was placed on an Orbit gyratory shaker at 50° C. and shaken for 20 hours at 250 RPM. At the end of this period, the contents of the flasks were filtered over glass microfiber filter paper, and the glucose concentration in the filtrate was measured by a Dionex Pulsed-Amperometric HPLC. The glucose concentration was related to the cellulose concentration in the pretreated feedstock to determine the glucose yield.

The results are summarized in TABLE 7.

After the first stage of reaction, little hemicellulose remained in the oat hulls. The glucose yield after the cellulose was hydrolyzed by cellulase was only 340 mg/g.

After the second stage of pretreatment reaction, the glucose yield is over 85% higher than that of the first stage. The second stage pretreatment reaction therefore provided a significant enhancement of the hydrolysis performance. The two stage pretreatment results in a glucose yield within 6% of that after the single stage reaction of oat hulls described in EXAMPLE 4.

These results ran exactly opposite to the teachings of Knappert, et al, who concluded that a material with low hemicellulose content does not have an improved digestibility by cellulase enzymes after pretreatment reaction. In the present example, after the first stage of reaction, very little hemicellulose remained in the oat hulls, yet the second stage reaction increased the digestibility significantly. Knappert et al taught that such a low-hemicellulose material should not respond well to pretreatment reaction. The present invention teaches the opposite.

TABLE 7

TWO STAGE PRETREATMENT REACTION OF OAT HULLS

| Pretreatment reaction | Hemicellulose content before this stage (%) | Glucose yield (mg/g cellulose) |
|---|---|---|
| Two stage | 3.0 | 645 |
| First stage | 22.0 | 340 |
| Single stage (EXAMPLE 4) | 22.0 | 685 |

EXAMPLE 6: LARGE SCALE PRETREATMENT REACTION WITH OAT HULLS

A large scale pretreatment of oat hulls was carried out using a Werner-Pflederer twin-screw extruder (Ramsey, N.J.). After milling in a Wiley mill, the oat hulls were slurried to a 30% solids concentration in 1% sulfuric acid (pH 0.7 to 1.2). The slurry was fed to the extruder at a rate of 10 pounds per hour and the pressure was 500 psig. The extruder was maintained at 230° C. with live steam injection. At the average feed rate, the material passed through the extruder within 30 seconds. The extruded oat hulls were collected and washed with water to remove dissolved material, then filtered over glass microfiber filter paper.

The cellulose content of the extruded oat hulls was measured using the methods of EXAMPLE 1.

The extruded oat hulls were subjected to hydrolysis by cellulase as follows. A sample of the extruded oat hulls corresponding to 0.05 grams of cellulose was added to a 25 ml flask with 4.9 grams of 0.05 M sodium citrate buffer, pH 4.8. Iogen Cellulase (140 FPU/ml) and Novozym 188 beta-glucosidase (1440 BGU/ml) were added to the flask in an amount corresponding to 9 FPU/gram cellulose and 125 BGU/gram cellulose. The small amount of glucose carried into the flask with the beta-glucosidase was taken into account.

Each flask was placed on an Orbit gyratory shaker at 50° C. and shaken for 20 hours at 250 RPM. At the end of this period, the contents of the flask were filtered over glass microfiber filter paper, and the glucose concentration in the filtrate was measured by a Dionex Pulse-Amperometric HPLC. The glucose concentration was related to the cellulose concentration of the extruded oat hulls to determine the glucose yield.

The results are listed in TABLE 8. The glucose yield from the large scale pretreatment reaction of oat hulls was slightly (8%) less than that from the laboratory scale pretreatment in EXAMPLE 4. This indicates that the oat hull pretreatment reaction can be run on a large scale, as optimization of the extrusion operation will no doubt overcome the 8% advantage of the laboratory pretreatment reaction.

TABLE 8

GLUCOSE YIELD FROM PRETREATED OAT HULLS

| Pretreatment | Glucose (mg/g cellulose) |
|---|---|
| Extruder | 630 |
| Bomb (EXAMPLE 4) | 685 |

EXAMPLE 7: LARGE SCALE PRETREATMENT OF HARDWOOD

A sample of aspen wood was pretreated using the steam explosion device and technique described by FOODY, U.S. Pat. No. 4,461,648. The resulting pretreated material was washed with water and is denoted as "Steam exploded hardwood". The cellulose content of the steam exploded hardwood was measured using the methods of EXAMPLE 1.

The steam exploded hardwood was subjected to hydrolysis by cellulase enzyme as follows. A sample of the steam exploded hardwood corresponding to 0.05 grams of cellulose was added to a 25 ml flask with 4.9 grams of 0.05 molar sodium citrate buffer, pH 4.8. Iogen Cellulase (140 FPU/ml) and Novozym 188 beta-glucosidase (1440 BGU/ml) were added to the flask in an amount corresponding to 9 FPU/gram cellulose and 125 BGU/gram cellulose. The small amount of glucose carried into the flask with the beta-glucosidase was taken into account.

Each flask was placed on an Orbit gyratory shaker at 50° C. and shaken for 20 hours at 250 RPM. At the end of this period, the contents of the flask were filtered over glass microfiber filter paper, and the glucose concentration in the filtrate was measured by a Dionex Pulsed-Amperometric HPLC. The glucose concentration was related to the cellulose concentration of the steam exploded hardwood to determine the glucose yield.

The results are listed in TABLE 9. The performance of the hardwood reacted using the large scale device is within 2%, by weight, of that using the laboratory device. In this case, the large scale use of steam explosion has been extensively optimized and can match the laboratory results.

TABLE 9

PRETREATMENT REACTION OF HARDWOOD

| Device | Glucose yield (mg/g cellulose) |
|---|---|
| Steam explosion | 415 |
| Laboratory (EXAMPLE 4) | 425 |

EXAMPLE 8: EFFECT OF TEMPERATURE ON SINGLE-STAGE AND TWO-STAGE PRETREATMENT REACTION OF OAT HULLS

This example demonstrates the use of a range of temperatures with both single stage and two-stage pretreatment reactions of oat hulls.

For the single stage reactions, samples of 0.28 grams of oat hulls were placed in 7 grams of 1% sulfuric acid (pH 0.6) in a sealed stainless steel "bomb" reactor as described in EXAMPLE 4. Five bombs of identical contents were set up and the reaction products combined to produce a pool of adequate quantity with which to work. The bombs were placed in a preheated oil bath, then removed and cooled by placing them in tap water.

The temperatures and times in the oil bath were, as follows:

(1) 235° C., 50 seconds; (2) 180° C., 6 minutes; (3) 170° C., 8 minutes.

The contents of the bombs were removed by rinsing with tap water, and then vacuum-filtered over glass microfiber filter paper. The filter cakes were washed with tap water and air dried. The cellulose concentration in the solids was determined by dissolution of aliquots in 70% sulfuric acid, as described in EXAMPLE 1.

For the two stage reactions, the first stage was carried out by placing samples of 4 grams of Wiley-milled oat hulls in 96 grams of 1% sulfuric add (pH 0.6) in a 250 ml flask. The contents of the flasks were gently mixed, and then the flasks were placed in a steam autoclave at 121° C. for 40 minutes. The flasks were then cooled and the contents were vacuum-filtered over glass microfiber filter paper. The filter cakes were washed with tap water and air dried. The cellulose, xylan, and arabinan concentrations in the solids were determined by dissolution of aliquots in 70% sulfuric acid, as described in EXAMPLE 1.

The second stage was carried out by placing samples of 0.28 grams of material from the first stage in 7 grams of 1% sulfuric acid (pH 0.6) in a sealed stainless steel "bomb" reactor as described in EXAMPLE 4. Five bombs of identical contents were set up and the reaction products combined to produce a pool of adequate quantity to work with. The bombs were placed in a preheated oil bath, then removed and cooled by placing them in tap water.

The temperatures and times in the oil bath matched those for the single stage reaction: (1) 235° C., 50 seconds; (2) 180° C., 6 minutes; (3) 170° C., 8 minutes.

The contents of the bombs were removed by rinsing with tap water, and then vacuum-filtered over glass microfiber filter paper. The filter cakes were washed with tap water and air dried. The cellulose concentration in the solids was determined by dissolution of aliquots in 70% sulfuric acid, as described in EXAMPLE 1.

Feedstocks after one or two stages of reaction were subjected to cellulase enzyme hydrolysis as follows. A sample of the reacted solids corresponding to 0.05 grams of cellulose was added to a 25 ml flask with 4.9 grams of 0.05 molar sodium citrate buffer, pH 4.8. IOGEN Cellulase (140 FPU/ml) and NOVOZYM 188 beta-glucosidase (1440 BGU/ml) were added to the flask in an amount corresponding to 9 FPU/gram cellulose and 125 BGU per gram cellulose. The small amount of glucose carried into the flask with the beta-glucosidase was taken into account.

Each flask was placed on an Orbit gyratory shaker at 50° C. and shaken for 20 hours at 250 RPM. At the end of this period, the contents of the flasks were filtered over glass microfiber filter paper, and the glucose concentration in the filtrate was measured by a Dionex Pulsed-Amperometric HPLC. The glucose concentration was related to the cellulose concentration in the pretreated feedstock to determine the glucose yield.

The results are summarized in TABLE 10.

Using a single stage reaction, the glucose yield is almost as high at 180° C. as at the optimum temperature. The glucose yield drops as the temperature is decreased from 180° C. to 170° C.

The two stage reaction has the same temperature profile as the single stage pretreatment reaction, with a similar performance at 180° C. and the optimum temperature, and a drop in performance below 180° C. Glucose yields in the two-stage reaction were 15% below those with the single stage reaction.

TABLE 10

EFFECT OF TEMPERATURE ON GLUCOSE YIELD FROM OAT HULLS

| Pretreatment | Reaction Temperature (C.) | Reaction Time (sec) | Glucose yield (mg/g cellulose) | Relative Glucose yield |
|---|---|---|---|---|
| Single stage | 235 | 50 | 685 | 100 |
| Single stage | 180 | 360 | 660 | 96 |
| Single stage | 170 | 480 | 555 | 81 |
| Two stages | 235* | 50 | 575 | 84 |
| Two stages | 180* | 360 | 560 | 82 |
| Two stages | 170* | 480 | 485 | 71 |

*Following a first stage at 121° C.

While preferred embodiments of our invention have been shown and described, the invention is to be defined solely by the scope of the appended claims, including any equivalent for each recited claim element that would occur to one of ordinary skill and would not be precluded by prior art considerations.

We claim:

1. An improved process for pretreating a lignocellulosic feedstock for conversion to fuel ethanol, consisting essentially of the following steps:

a. Choosing a selectively bred feedstock, comprised of at least hemicellulose and cellulose, on the basis of an increased ratio of arabinan plus xylan to total nonstarch polysaccharides (AX/NSP) over a starting feedstock material, wherein the feedstock consists of corn, oats, wheat, sugar cane, or a component thereof, wherein the feedstock contains less than 10% starch; and b. Reacting the selectively bred feedstock at conditions which disrupt its fiber structure and effect an hydrolysis of a portion of the hemicellulose and cellulose, in order to create a pretreated feedstock with increased accessibility to being digested, during a treatment with cellulase enzymes.

2. A process according to claim 1 wherein the feedstock has been selectively bred to have an AX/NSP level of greater than about 0.39.

3. A process according to claim 1 wherein the reaction step is carried out by subjecting the selectively bred feedstock to an average temperature of 180° C. to 270° C., at pH 0.5 to 2.5, for a period of 5 seconds to 60 minutes.

4. A process according to claim 3 wherein the reaction step is carried out by subjecting the selectively bred feedstock to an average temperature of 220° C. to 270° C., at pH 0.5 to 2.5 for a period of 5 seconds to 120 seconds.

5. A process according to claim 1 wherein the reaction step is carried out in two stages, with the first stage at an average temperature below 180° C. and the second stage at an average temperature above 180° C.

6. A process according to claim 5 wherein the first stage of the reaction step is carried out at an average temperature of 60° C. to 140° C. for 0.25 to 24 hours at pH 0.5 to 2.5.

7. A process according to claim 6 wherein the first stage of the reaction step is carried out at an average temperature of 100° C. to 130° C. for 0.5 to 3 hours at pH 0.5 to 2.5.

8. A process according to claim 5 wherein the second stage of the reaction step is carried out by subjecting the selectively bred feedstock to an average temperature of 180° C. to 270° C., at pH 0.5 to 2.5, for a period of 5 seconds to 60 minutes.

9. A process according to claim 8 wherein the second stage of the reaction step is carried out by subjecting the chosen feedstock at an average temperature of 220° C. to 270° C., at pH 0.5 to 2.5, for a period of 5 seconds to 120 seconds.

10. A process according to claim 1 wherein the selectively bred feedstock is slurried in water during the reaction step.

11. A process according to claim 1 wherein the selectively bred feedstock is free of externally-added moisture during the reaction step.

12. A process according to claim 1 wherein the pretreatment is carried out with a steam explosion or extrusion device during the reaction step.

13. An improved process for pretreating a lignocellulosic feedstock for conversion to fuel ethanol, consisting essentially of the following steps:
   a. Choosing a selectively bred feedstock, comprised of at least hemicellulose and cellulose, on the basis of an increased ratio of arabinan plus xylan to total nonstarch polysaccharides (AX/NSP) over a starting feedstock material, wherein the feedstock consists of a C4 perennial grass; and
   b. Reacting the selectively bred feedstock at conditions which disrupt its fiber structure and effect an hydrolysis of a portion of the hemicellulose and cellulose, in order to create a pretreated feedstock with increased accessibility to being digested, during a treatment with cellulase enzymes.

14. A process according to claim 13, wherein the feedstock consists of a C4 perennial grass that is switch grass, miscanthus, cord grass, or rye grass.

15. A process according to claim 14 wherein the feedstock has been selectively bred to have an AX/NSP level of greater than about 0.39.

16. A process according to claim 14 wherein the reaction step is carried out by subjecting the selectively bred feedstock to an average temperature of 180° C. to 270° C., at pH 0.5 to 2.5, for a period of 5 seconds to 60 minutes.

17. A process according to claim 16 wherein the reaction step is carried out by subjecting the selectively bred feedstock to an average temperature of 220° C. to 270° C., at pH 0.5 to 2.5 for a period of 5 seconds to 120 seconds.

18. A process according to claim 14 wherein the reaction step is carried out in two stages, with the first stage at an average temperature below 180° C. and the second stage at an average temperature above 180° C.

19. A process according to claim 18 wherein the first stage of the reaction step is carried out at an average temperature of 60° C. to 140° C. for 0.25 to 24 hours at pH 0.5 to 2.5.

20. A process according to claim 19 wherein the first stage of the reaction step is carried out at an average temperature of 100° C. to 130° C. for 0.5 to 3 hours at pH 0.5 to 2.5.

21. A process according to claim 18 wherein the second stage of the reaction step is carried out by subjecting the selectively bred feedstock to an average temperature of 180° C. to 270° C., at pH 0.5 to 2.5, for a period of 5 seconds to 60 minutes.

22. A process according to claim 21 wherein the second stage of the reaction step is carried out by subjecting the chosen feedstock at an average temperature of 220 °C. to 270° C., at pH 0.5 to 2.5, for a period of 5 seconds to 120 seconds.

23. A process according to claim 13 wherein the selectively bred feedstock is slurried in water during the reaction step.

24. A process according to claim 13 wherein the selectively bred feedstock is free of externally-added moisture during the reaction step.

25. A process according to claim 13 wherein the pretreatment is carried out with a steam explosion or extrusion device during the reaction step.

26. A process for converting a lignocellulosic feedstock to ethanol, the process consisting essentially of the following steps:
   a. Choosing a selectively bred feedstock, comprised of at least hemicellulose and cellulose on the basis of an increased ratio of arabinan plus xylan to total nonstarch polysaccharides (AX/NSP) over a starting feedstock material, wherein the feedstock is corn, oats, wheat, sugar cane, or a component thereof, and wherein the feedstock contains less than 10% starch; and
   b. Reacting the selectively bred feedstock at conditions which disrupt its fiber structure and effect an hydrolysis of a portion of the hemicellulose and cellulose, in order to create a pretreated feedstock with increased accessibility to being digested, during a treatment with cellulase enzymes; and
   c. Hydrolyzing the pretreated feedstock to sugars by using cellulase enzymes; and
   d. Fermenting the resulting sugars to ethanol; and
   e. Recovering the ethanol.

27. A process according to claim 26 wherein the feedstock has been selectively bred to have an AX/NSP that is greater than about 0.39.

28. A process for converting a lignocellulosic feedstock to ethanol, the process consisting essentially of the following steps:
   a. Choosing a selectively bred feedstock, comprised of at least hemicellulose and cellulose, on the basis of an increased ratio of arabinan plus xylan to total nonstarch polysaccharides (AX/NSP) over a starting feedstock material, wherein the feedstock is a C4 perennial grass; and
   b. Reacting the selectively bred feedstock at conditions which disrupt its fiber structure and effect an hydrolysis of a portion of the hemicellulose and cellulose, in order to create a pretreated feedstock with increased accessibility to being digested, during a treatment with cellulase enzymes; and
   c. Hydrolyzing the pretreated feedstock to sugars by using cellulase enzymes; and d. Fermenting the resulting sugars to ethanol; and e. Recovering the ethanol.

29. A process according to claim 28, wherein the feedstock consists of a C4 perennial grass that is switch grass, miscanthus, cord grass, or rye grass.

30. A process according to claim 29 wherein the feedstock has been selectively bred to have an AX/NSP that is greater than about 0.39.

31. A process for converting a lignocellulosic feedstock to glucose, consisting essentially of the following steps:

a. Choosing a selectively bred feedstock, comprised of at least hemicellulose and cellulose, on the basis of an increased ratio of arabinan plus xylan to total nonstarch polysaccharides (AX/NSP) over a starting feedstock material, wherein the feedstock consists of corn, wheat, oats, sugar cane, or a component thereof, and wherein the feedstock contains less than 10% starch; and b. Reacting the selectively bred feedstock to conditions which disrupt its fiber structure and effect an hydrolysis of a portion of the hemicellulose and cellulose, in order to create a pretreated feedstock with increased accessibility to being digested, during a treatment with cellulase enzymes; and c. Hydrolyzing at least 40% of the cellulose in the pretreated feedstock to glucose by using cellulase enzymes.

32. A process according to claim 31 wherein the feedstock has been selectively bred to have an AX/NSP that is greater than about 0.39.

33. A process for converting a lignocellulosic feedstock to glucose, consisting essentially of the following steps:

a. Choosing a selectively bred feedstock, comprised of at least hemicellulose and cellulose, on the basis of an increased ratio of arabinan plus xylan to total nonstarch polysaccharides (AX/NSP) over a starting feedstock material, wherein the feedstock consists of a C4 perennial grass; and b. Reacting the selectively bred feedstock to conditions which disrupt its fiber structure and effect an hydrolysis of a portion of the hemicellulose and cellulose, in order to create a pretreated feedstock with increased accessibility to being digested, during a treatment with cellulase enzymes; and c. Hydrolyzing at least 40% of the cellulose in the pretreated feedstock to glucose by using cellulase enzymes.

34. A process according to claim 33, wherein the feedstock consists of a C4 perennial grass that is switch grass, miscanthus, cord grass, or rye grass.

35. A process according to claim 34 wherein the feedstock has been selectively bred to have an AX/NSP that is greater than about 0.39.

36. An improved process for pretreating a lignocellulosic feedstock for conversion to fuel ethanol, consisting essentially of the following steps:

a. Choosing a feedstock comprised of at least hemicellulose and cellulose, and characterized by a ratio of arabinan plus xylan to total nonstarch polysaccharides (AX/NSP) that is greater than 0.39, wherein the feedstock is not corn fiber; and b. Reacting the chosen feedstock at conditions which disrupt its fiber structure and effect an hydrolysis of a portion of the hemicellulose and cellulose, in order to create a pretreated feedstock with increased accessibility to being digested, during a treatment with cellulase enzymes.

37. A process according to claim 36 wherein the feedstock has a starch content of less than 10%.

38. A process according to claim 37 wherein the feedstock has a starch content of less than 7%.

39. A process according to claim 37 wherein the reaction step is carried out by subjecting the feedstock to an average temperature of 180° C. to 270° C., at pH 0.5 to 2.5, for a period of 5 seconds to 60 minutes.

40. A process according to claim 39 wherein the reaction step is carried out by subjecting the selectively bred feedstock to an average temperature of 220° C. to 270° C., at pH 0.5 to 2.5 for a period of 5 seconds to 120 seconds.

41. A process according to claim 37 wherein the reaction step is carried out in two stages, with the first stage at an average temperature below 180° C. and the second stage at an average temperature above 180° C.

42. A process according to claim 41 wherein the first stage of the reaction step is carried out at an average temperature of 60° C. to 140° C. for 0.25 to 24 hours at pH 0.5 to 2.5.

43. A process according to claim 42 wherein the first stage of the reaction step is carried out at an average temperature of 100° C. to 130° C. for 0.5 to 3 hours at pH 0.5 to 2.5.

44. A process according to claim 41 wherein the second stage of the reaction step is carried out by subjecting the selectively bred feedstock to an average temperature of 180° C. to 270° C., at pH 0.5 to 2.5, for a period of 5 seconds to 60 minutes.

45. A process according to claim 44 wherein the second stage of the reaction step is carried out by subjecting the chosen feedstock at an average temperature of 220° C. to 270° C., at pH 0.5 to 2.5, for a period of 5 seconds to 120 seconds.

46. A process according to claim 36 wherein the feedstock is slurried in water during the reaction step.

47. A process according to claim 36 wherein the feedstock is free of externally-added moisture during the reaction step.

48. A process according to claim 36 wherein the pretreatment is carried out with a steam explosion or extrusion device during the reaction step.

49. A process for converting a lignocellulosic feedstock to ethanol, the process consisting essentially of the following steps:

a. Choosing a feedstock, comprised of at least hemicellulose and cellulose, and characterized by a ratio of arabinan plus xylan to total nonstarch polysaccharides (AX/NSP) of greater than 0.39, wherein the feedstock is not corn fiber; and b. Reacting the feedstock at conditions which disrupt its fiber structure and effect an hydrolysis of a portion of the hemicellulose and cellulose, in order to create a pretreated feedstock with increased accessibility to being digested, during a treatment with cellulase enzymes; and c. Hydrolyzing the pretreated feedstock to sugars by using cellulase enzymes; and d. Fermenting the resulting sugars to ethanol; and e. Recovering the ethanol.

50. A process according to claim 49 wherein the feedstock has a starch content of less than 10%.

51. A process for converting a lignocellulosic feedstock to glucose, consisting essentially of the following steps:

a. Choosing a feedstock, comprised of at least hemicellulose and cellulose, characterized by a ratio of arabinan plus xylan to total nonstarch polysaccharides (AX/NSP) of greater than 0.39, wherein the feedstock is not corn fiber; and b. Reacting the feedstock at conditions which disrupt its fiber structure and effect an hydrolysis of a portion of the hemicellulose and cellulose, in order to create a pretreated feedstock with increased accessibility to being digested, during a treatment with cellulase enzymes; and c. Hydrolyzing at least 40% of the cellulose in the pretreated feedstock to glucose by using cellulase enzymes.

52. A process according to claim 51 wherein the feedstock has a starch content of less than 10%.

53. A process according to claim 52 wherein the feedstock has a starch content of less than 7%.

* * * * *